US005463115A

United States Patent [19]

Batal et al.

[11] Patent Number: 5,463,115

[45] Date of Patent: Oct. 31, 1995

[54] SULFONIMINES AS BLEACH CATALYSTS

[75] Inventors: David J. Batal, Secaucus, N.J.; Stephen A. Madison, Valley Cottage, N.Y.

[73] Assignee: Lever Brothers Company, Division of Conopco, Inc., New York, N.Y.

[21] Appl. No.: 731,839

[22] Filed: Jul. 16, 1991

Related U.S. Application Data

[62] Division of Ser. No. 494,713, Mar. 16, 1990, Pat. No. 5,041,232.

[51] Int. Cl.[6] .................................................. C07C 317/14

[52] U.S. Cl. .............................................. 562/430; 564/89

[58] Field of Search .................................... 562/430, 507, 562/556, 557, 602, 606; 560/10, 12, 150, 22; 558/413, 420, 431, 437, 449; 564/87, 90, 91, 92, 93, 96, 98, 99, 89

[56] References Cited

U.S. PATENT DOCUMENTS

| | | | |
|---|---|---|---|
| 3,245,913 | 4/1966 | Matzner | 252/99 |
| 4,412,934 | 11/1983 | Chung et al. | 252/186.38 |
| 4,948,809 | 8/1990 | Witte et al. | 514/538 |
| 4,948,810 | 8/1990 | Iwakuma et al. | 562/430 X |

FOREIGN PATENT DOCUMENTS

| | | |
|---|---|---|
| 1230785 | 8/1967 | Germany . |

OTHER PUBLICATIONS

Vishwakarma, L. C.; Stringer, O. D.; Davis, F. A. *Org. Synth.* 1987, 66, 203.

Davis et al., J.C.S. Chem. Comm. (1977), pp. 25–26.

Davis, et al., J. Org. Chem., (1988), vol. 53, pp. 2087–2089.

Davis, et al., J. Org. Chem. (1982), 47, 1774–1775.

Chemical Abstracts, vol. 81, 1974, Abstract No. 37363.

Chemical Abstracts, vol. 80, 1974, Abstract No. 11213.

Chemical Abstracts, vol. 108, 1974, Abstract No. 131281.

*Primary Examiner*—José G. Dees

*Attorney, Agent, or Firm*—Milton L. Honig

[57] ABSTRACT

Novel bleach catalysts, a method for bleaching substrates using these catalysts and detergent compositions containing the catalysts are reported. The catalysts are sulfonimines. Substrates such as fabrics may be bleached in an aqueous solution containing the sulfonimine and a peroxygen compound.

12 Claims, No Drawings

SULFONIMINES AS BLEACH CATALYSTS

This is a divisional application of Ser. No. 07/494,713 filed Mar. 16, 1990, now U.S. Pat. No. 5,041,232.

BACKGROUND OF THE INVENTION

1. Field of the Invention

The invention relates to novel bleach catalysts, compositions containing same and a method for using these catalysts in detergent compositions, especially for cleaning fabrics.

2. The Related Art

Many household and personal care products are formulated with an active oxygen-releasing material to effect removal of stain and soil. Oxygen-releasing materials have an important limitation; their activity is extremely temperature dependent. Temperatures in excess of 60° C. are normally required to achieve any bleach effectiveness in an aqueous wash system. Especially for cleaning fabrics, high temperature operation is both economically and practically disadvantageous.

The art has partially solved the aforementioned problem through the use of activators. These activators, also known as bleach precursors, often appear in the form of carboxylic acid esters. In an aqueous liquor, anions of hydrogen peroxide react with the ester to generate the corresponding peroxyacid which oxidizes the stained substrate. Commercial application of this technology is found in certain fabric bleaching detergent powders incorporating sodium nonanoyloxybenzene sulfonate. This activator is typical of a class that features a phenol sulfonate leaving group; see Chung et al. U.S. Pat. No. 4,412,934.

While carboxylic acid ester activators and the like are often effective, they are not catalytic. Once the ester has been perhydrolyzed it can no longer be recycled. Accordingly, relatively large amounts of activator are necessary. Amounts as high as 8% may be necessary in a detergent formulation for bleaching fabrics. Cost for these relatively expensive activators is of major concern at such levels.

Outside the context of consumer products, there have been reports of catalytic oxidizing agents. F. A. Davis and coworkers, in a series of articles, reported preparation of-a new class of stable oxidizing agents, namely 2-arenesulfonyl-3-aryl-oxaziridines. See Davis, Nadir, and Kluger, *J.C.S. Chem. Comm.* 1977, 25; Davis, Lamendola Jr., Nadir, Kluger, Sederjarn, Panunto, Billmers, Jenkins Jr., Turchi, Watson, Chen and Kimura, *J. Amer. Chem. Soc.* 1980, 102, 2000; and Davis, Chattopadhay, Towson, Lal and Reedy, *J. Org. Chem.* 1988, 53, 2087. These oxaziridines were prepared by peracid or monopersulfate oxidation of a corresponding sulfonimine under alkaline conditions. In late 1988, Davis published a paper entitled "Selective Catalytic Oxidation of Sulfides to Sulfoxides Using N-sulfonyloxaziridines" *J. Org. Chem.* 1988, 53, 5004. Therein described is a system where sulfonimine reacts with monopersulfate to generate an in situ oxaziridine in a toluene-water biphasic mixture. Oxaziridine then coverts the sulfide to a sulfoxide and generates starting sulfonimine, thereby rendering the process catalytic in nature. Beyond use as a synthetic tool, there is no suggestion of any possible application for sulfonimine chemistry to the problem of removing stain in consumer applications, such as in cleaning fabrics.

It is an object of the present invention to provide novel bleach catalysts and detergent compositions containing such catalysts that operate over a wide temperature range including that of under 60° C.

It is another object of the present invention to provide novel bleach catalysts which are effective at relatively low concentrations thereby achieving a quite cost effective stain removal system.

A further object of the present invention is to provide a method for bleaching stained substrates such as clothes, household hard surfaces including sinks, toilets and the like, and even dentures.

Other objects of the present invention will become apparent through the following summary, detailed discussion and examples.

SUMMARY OF THE INVENTION

A bleaching composition is provided comprising:

(i) from about 1 to about 60% by weight of a peroxygen compound;

(ii) from about 0.05 to about 10% of an oxygen transfer agent whose structure is:

$$R^1R^2C{=}NSO_2R^3$$

wherein:

$R^1$ may be a substituted or unsubstituted radical selected from the group consisting of hydrogen, phenyl, aryl, heterocyclic ring, alkyl and cycloalkyl radicals;

$R^2$ may be a substituted or unsubstituted radical selected from the group consisting of hydrogen, phenyl, aryl, heterocyclic ring, alkyl, cycloalkyl, $R^1C{=}NSO_2R^3$, nitro halo, cyano, alkoxy, keto, carboxylic, and carboalkoxy radicals;

$R^3$ may be a substituted or unsubstituted radical selected from the group consisting of phenyl, aryl, heterocyclic ring, alkyl, cycloalkyl, nitro, halo and cyano radicals;

$R^1$ with $R^2$ and $R^2$ with $R^3$ may respectively together form a cycloalkyl, heterocyclic, and aromatic ring system; and (iii) from about 0.5 to 50% of a surfactant.

Additionally, there is provided a method for bleaching a stained substrate comprising the step of applying to the stained substrate an aqueous solution comprising a peroxygen compound and an oxygen transfer agent whose structure is $R^1R^2C{=}NSO_2R^3$, with radical groups as defined above, the mole ratio of peroxygen compound to oxygen transfer agent being from about 250:1 to about 1:2.

Certain novel compounds are also provided whose structure is $R^1R^2C{=}NSO_2R^3$ having radical groups as defined above with the proviso that at least one of $R^1$, $R^2$, $R^3$ is substituted with a water-solubilizing functional group. Typical water-solubilizing groups include carboxylic acid, phosphoric acid, phosphonic acid, sulfuric acid, sulfonic acid, and, especially, their salt derivatives.

DETAILED DESCRIPTION.

It has been found that sulfonimines can operate as catalysts on peroxygen compounds to transfer active oxygen to stains. Consumer and industrial articles can effectively be bleached to remove stains present on such articles. Thus, sulfonimine chemistry is more than a synthetic curiosity as in the conversion of sulfides to sulfoxides reported by Davis et al. Unlike the Davis et al biphasic system that requires an organic solvent, sulfonimines can be devised for use in completely aqueous wash systems.

Sulfonimines covered by the present invention are those whose structure is:

$$R^1R^2C{=}NSO_2R^3$$

wherein:

$R^1$ may be a substituted or unsubstituted radical selected from the group consisting of hydrogen, phenyl, aryl, heterocyclic ring, alkyl, and cycloalkyl radicals;

$R^2$ may be a substituted or unsubstituted radical selected from the group consisting of hydrogen, phenyl, aryl, heterocyclic ring, alkyl, cycloalkyl, $R^1C{=}NSO_2R^3$nitro, halo, cyano, alkoxy, keto, carboxylic and carboalkoxy radicals;

$R^3$ may be a substituted or unsubstituted radical selected from the group consisting of phenyl, aryl, heterocyclic ring, alkyl, cycloalkyl, nitro, halo, and cyano radicals; and $R^1$ with $R^2$ and $R^2$ with $R^3$ may respectively together form a cycloalkyl, heterocyclic or aromatic ring system.

Often advantageous are sulfonimines having at least one of $R^1$, $R^2$, $R^3$ substituted with a water-solubilizing functional group These functional groups may be selected from carboxylates, phosphates, phosphonates, sulfates, sulfonates in acid or salt form. Suitable salts include those whose counterions are selected from alkali metal, ammonium, and $C_2$–$C_6$ alkanolammonium anions.

Amine functional groups may also be incorporated into $R^1$, $R^2$ or $R^3$ to provide water-solubilization of the sulfonimines. An example combining the amine and heterocyclic structure is that of pyridine.

A water-solubilizing functional group is one which renders the sulfonimines soluble to the extent of at least 2 mg/l, preferably at least 25 mg/l, optimally at least 250 mg/l by weight in water at 25° C.

Heterocyclic rings according to this invention include cycloaliphatic and cycloaromatic type radicals incorporating an oxygen, sulfur and/or nitrogen atom within the ring system. Representative nitrogen heterocycles include pyridine, morpholine, pyrrole, imidazole, triazole, tetrazole, pyrrolidine, piperidine and piperazine. Suitable oxygen heterocycles include furan, tetrahydrofuran and dioxane. Sulfur heterocycles may include thiophene and tetrahydrothiophene. Among the various heterocycles, it has been found that those incorporating nitrogen are the most active.

The term "substituted" is defined in relation to $R^1$, $R^2$, $R^3$ as a substituent which is a nitro, halo, cyano, $C_1$–$C_{20}$ alkyl, amino, aminoalkyl, thioalkyl, sulfoxyalkyl, carboxyester, hydroxy, $C_1$–$C_{20}$ alkoxy, polyalkoxy and $C_1$–$C_{40}$ quaternary di- or trialkylammonium function.

Novel sulfonimine compounds are described below wherein $R^1$ is hydrogen, $R^2$ is phenyl with an X substituent, and $R^3$ is phenyl with a Y substituent. Very often X and Y groups are water-solubilizing groups, most commonly being carboxylic acid or salts thereof. Representative structures are as follows:

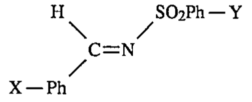

| | X | Y |
|---|---|---|
| SULF 1 | 4-$CO_2H$ | 4-Cl |
| SULF 2 | 4-$CO_2H$ | H |
| SULF 3 | 4-Cl | 4-$CO_2H$ |
| SULF 4 | H | 4-$CO_2H$ |
| SULF 5 | 4-$CO_2H$ | 4-$CO_2H$ |
| SULF 6 | 4-$CO_2H$ | 3-$NO_2$ |
| SULF 7 | 4-CN | 4-$CO_2H$ |
| SULF 8 | 4-OMe | 4-$CO_2H$ |
| SULF 9 | 3-OH | 4-Cl |

-continued

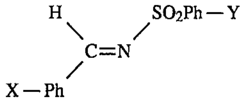

| | X | Y |
|---|---|---|
| SULF 10 | 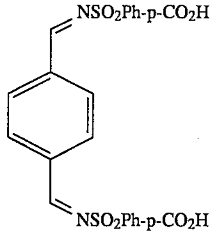 | |

Illustrative of cycloaromatic and of heterocyclic nitrogen ring sulfonimines are the respective SULF 11 and SULF 12 whose structures are outlined below.

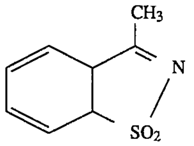

SULF 11

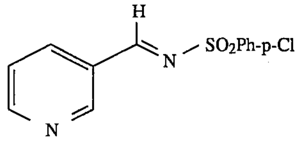

SULF 12

The following further compounds are illustrative of sulfonimines within the present invention.

N-Benzylidenebenzenesulfonamide
N-(4-Methylsulfinylbenzylidene)benzenesulfonamide
N-(4-Methylsulfonylbenzylidene)benzenesulfonamide
N-(3-Pyridinylmethylene)benzenesulfonamide
N-(4-Pyridinylmethylene)benzenesulfonamide
N-(2-Pyridinylmethylene)benzenesulfonamide
N-Benzylidene-3-pyridinesulfonamide
3-Trimethylammoniomethyl-1,2-benzisothiazole-1,1-dioxide chloride salt
1,2-Benzisothiazole-1,1-dioxide
N-(N-Methyl-3-pyridinylmethylene)benzenesulfonamide chloride salt
N-(4-Trimethylammoniobenzylidene)benzenesulfonamide chloride salt
N-Benzylidene-4-trimethylammoniobenzenesulfonamide chloride salt
N-(4-Cholyloxycarbonylbenzylidene)benzenesulfonamide chloride salt
N-Benzylidene-4-cholyloxycarbonylbenzenesulfonamide chloride salt
N-(4-Sulfoethylcarbonylbenzylidene)benzenesulfonamide sodium salt
N-(-Methylbenzylidene)benzenesulfonamide
Methyl N-(p-tolylsulfonyl)iminoacetate
Phenylsulfonyliminoacetic acid
N-Isopropylidenebenzenesulfonamide
N-Benzylidenemethanesulfonamide
N-(4-Carboxybenzylidene)methanesulfonamide
N-Benzylidenetrifluoromethanesulfonamide
N-(2,2,3,3,4,4,4-Heptafluorobutylidene)benzenesulfonamide N-(4-Dimethylsulfoniumbenzylidene)benzenesulfonamide chloride salt N-(2-Furfurylidene)-4-carboxybenzenesulfonamide N-(2-Pyrrolylmethylene)benzenesulfonamide N-(4-Phenoxycarbonylbenzylidene)-4-carboxybenzenesulfonamide N-(2,6-Dicarboxy-4-pyridinylmethylene)benzenesulfonamide disodium salt The foregoing oxygen transfer agents may be incorporated into detergent bleach compositions along with a further essential component which is a peroxygen compound capable of yielding peroxide anion in an aqueous solution.

Amounts of oxygen transfer agent suitable for the present invention may range from about 0.05 to 10%, preferably from about 0.2 to 5%, optimally between about 0.5% and 1.5% by weight of the composition.

The peroxygen compound may be present from about 1% to 65%, preferably from about 1.5% to 25%, optimally between about 2% and 10% by weight.

The molar ratio of peroxide anion (or a peroxygen compound generating the equivalent amount of peroxide anion) to oxygen transfer agent will range from about 250:1 to 1:2, preferably about 100:1 to 1:1, optimally between about 25:1 to 2:1.

Peroxide anion sources are well known in the art. They include the alkali metal peroxides, organic peroxides such as urea peroxide, and inorganic persalts, such as the alkali metal perborates, percarbonates, perphosphates, persilicates and persulfates. Mixtures of two or more such compounds may also be suitable. Particularly preferred are sodium perborate tetrahydrate and, especially, sodium perborate monohydrate. Sodium perborate monohydrate is preferred because it has excellent storage stability while also dissolving very quickly in aqueous solutions.

Alkylhydroperoxides are another suitable class of peroxygen compounds. Examples of these materials include cumene hydroperoxide and t-butyl hydroperoxide.

Organic peroxy acids may also be suitable as the peroxygen compound. Such materials have a general formula:

$$HO-O-\overset{\displaystyle O}{\overset{||}{C}}-R-Y$$

wherein R is an alkylene or substituted alkylene group containing from 1 to about 22 carbon atoms or a phenylene or substituted phenylene group, and Y is hydrogen, halogen, alkyl, aryl or $$-\overset{\displaystyle O}{\overset{||}{C}}-OH \text{ or } -\overset{\displaystyle O}{\overset{||}{C}}-O-OH$$

The organic peroxy acids usable in the present invention can contain either one or two peroxy groups and can be either aliphatic or aromatic. When the organic peroxy acid is aliphatic, the unsubstituted acid has the general formula:

$$HO-O-\overset{\displaystyle O}{\overset{||}{C}}-(CH_2)_n-Y$$

where Y can be, for example, H, $CH_3$, $CH_2C_1$, COOH, or COOOH; and n is an integer from 1 to 20.

When the organic peroxy acid is aromatic, the unsubstituted acid has the general formula:

$$HO-O-\overset{\displaystyle O}{\overset{||}{C}}-C_6H_4-Y$$

wherein Y is hydrogen, alkyl, alkylhalogen, halogen, or COOH or COOOH.

Typical monoperoxy acids useful herein include alkyl peroxy acids and aryl peroxy acids such as:

(i) peroxybenzoic acid and ring-substituted peroxybenzoic acids, e.g. peroxy-α-naphthoic acid;

(ii) aliphatic, substituted aliphatic and arylalkyl monoperoxy acids, e.g. peroxylauric acid, peroxystearic acid, and N,N-phthaloylaminoperoxycaproic acid.

Typical diperoxy acids useful herein include alkyl diperoxy acids and aryldiperoxy acids, such as:

(iii) 1,12-diperoxydodecanedioic acid;

(iv) 1,9-diperoxyazelaic acid;

(v) diperoxybrassylic acid; diperoxysebacic acid and diperoxyisophthalic acid;

(vi) 2-decyldiperoxybutane-1,4-dioic acid;

(vii) 4,4'-sulfonylbisperoxybenzoic acid.

Particularly preferred organic acids are peracetic acid, monoperoxyphthalic acid (magnesium salt hexahydrate), and diperoxydodecanedioic acid. Under certain circumstances, hydrogen peroxide itself may directly be employed as the peroxygen compound.

Bleach systems of the present invention may be employed for a wide variety of purposes, but are especially useful in the cleaning of laundry. When intended for such purpose, the peroxygen compound and oxygen transfer agent of the present invention will usually also be combined with surface-active materials, detergency builders and other known ingredients of laundry detergent formulations.

The surface-active material may be naturally derived, or synthetic material selected from anionic, nonionic, amphoteric, zwitterionic, cationic actives and mixtures thereof. Many suitable actives are commercially available and are fully described in the literature, for example in "Surface Active Agents and Detergents", Volumes I and II, by Schwartz, Perry and Berch. The total level of the surface-active material may range up to 50% by weight, preferably being from about 0.5 to 40% by weight of the composition, most preferably 4 to 25%.

Synthetic anionic surface-actives are usually water-soluble alkali metal salts of organic sulphates and sulphonates having alkyl radicals containing from about 8 to about 22 carbon atoms.

Examples of suitable synthetic anionic detergent compounds are sodium and ammonium alkyl sulphates, especially those obtained by sulphating higher ($C_8$–$C_{18}$) alcohols produced for example from tallow or coconut oil; sodium and ammonium alkyl ($C_9$–$C_{20}$) benzene sulphonates, sodium alkyl glyceryl ether sulphates, especially those ethers of the higher alcohols derived from tallow or coconut oil and synthetic alcohols derived from petroleum; sodium coconut oil fatty acid monoglyceride sulphates and sulphonates; sodium and ammonium salts of sulphuric acid esters of higher ($C_9$–$C_{18}$) fatty alcohol-alkylene oxide, particularly ethylene oxide, reaction products; the reaction products of fatty acids such as coconut fatty acids esterified with isethionic acid and neutralized with sodium hydroxide; sodium and ammonium salts of fatty acid amides of methyl taurine; alkane monosulphonates such as those derived by reacting alpha-olefins ($C_8$–$C_{20}$) with sodium bisulphite and those derived by reacting paraffins with $SO_2$ and $Cl_2$ and then hydrolyzing with a base to produce a random sulphonate; sodium and ammonium $C_7$–$C_{12}$ dialkyl sulfosuccinates; and olefin sulphonates, which term is used to describe the material made by reacting olefins, particularly $C_{10}$–$C_{20}$ alpha-olefins, with $SO_3$ and then neutralizing and hydrolyzing the reaction product. The preferred anionic detergent compounds are sodium ($C_{11}$–$C_{15}$) alkylbenzene sulphonates, sodium ($C_{16}$–$C_{18}$) alkyl sulphates and sodium ($C_{16}$–$C_{18}$) alkyl ether sulphates.

Examples of suitable nonionic surface-active compounds which may be used, preferably together with the anionic surface-active compounds, include in particular the reaction products of alkylene oxides, usually ethylene oxide, with alkyl ($C_6$–$C_{22}$) phenols, generally 5–25 EO, i.e. 5–25 units of ethylene oxide per molecule; the condensation products of aliphatic ($C_8$–$C_{18}$) primary or secondary linear or branched alcohols with ethylene oxide, generally 2–30 EO, and products made by condensation of ethylene oxide with the reaction products of propylene oxide and ethylene diamine. Other so-called nonionic surface-actives include alkyl polyglycosides, long chain tertiary amine oxides, long chain tertiary phosphine oxides and dialkyl sulphoxides.

Amphoteric or zwitterionic surface-active compounds can also be used in the compositions of the invention but this is not normally desired owing to their relatively high cost. If any amphoteric or zwitterionic detergent compounds are used, it is generally in small amounts in compositions based on the much more commonly used synthetic anionic and nonionic actives.

Soaps may also be incorporated into the compositions of the invention, preferably at a level of less than 30% by weight. They are particularly useful at low levels in binary (soap/anionic) or ternary mixtures together with nonionic or mixed synthetic anionic and nonionic compounds. Soaps which are used are preferably the sodium, or less desirably potassium, salts of saturated or unsaturated $C_{10}$–$C_{24}$ fatty acids or mixtures thereof. The amount of such soaps can be varied between about 0.5% and about 25% by weight, with lower amounts of about 0.5% to about 5% being generally sufficient for lather control. Amounts of soap between about 2% and about 20%, especially between about 5% and about 15%, are used to give a beneficial effect on detergency. This is particularly valuable in compositions used in hard water when the soap acts as a supplementary builder.

The detergent compositions of the invention will normally also contain a detergency builder. Builder materials may be selected from (1) calcium sequestrant materials, (2) precipitating materials, (3) calcium ion-exchange materials and (4) mixtures thereof.

In particular, the compositions of the invention may contain any one of the organic or inorganic builder materials, such as sodium or potassium tripolyphosphate, sodium or potassium pyrophosphate, sodium or potassium orthophosphate, sodium carbonate, the sodium salt of nitrilotriacetic acid, sodium citrate, carboxymethylmalonate, carboxymethyloxysuccinate, tartrate mono- and di- succinates, oxydisuccinate, crystalline or amorphous aluminosilicates and mixtures thereof.

Polycarboxylic homo- and co-polymers may also be included as builders and to function as powder structurants or processing aids. Particularly preferred are polyacrylic acid (available under the trademark Acrysol from the Rohm and Haas Company) and acrylic-maleic acid copolymers (available under the trademark Sokalan from the BASF Corporation) and alkali metal or other salts thereof.

These builder materials may be present at a level of, for example, from about 1 to 80% by weight, preferably from 10 to 60% by weight.

Upon dispersal in a wash water, the initial amount of peroxygen compound should range anywhere from about 0.05 to about 250 ppm active oxygen per liter of water, preferably between about 1 to 50 ppm. Within the wash media the amount of oxygen transfer agent initially present should be from about 0.01 to about 300 ppm, preferably from about 5 to 100 ppm. Surfactant should be present in the wash water from about 0.05 to 1.0 grams per liter, preferably from 0.15 to 0.20 grams per liter. When present, the builder amount will range from about 0.1 to 3.0 grams per liter.

Apart from the components already mentioned, the detergent compositions of the invention can contain any of the conventional additives in the amounts in which such materials are normally employed in detergent compositions. Examples of these additives include lather boosters such as alkanolamides, particularly the monoethanolamides derived from palmkernel fatty acids and coconut fatty acids, lather depressants such as alkyl phosphates and silicones, anti-redeposition agents such as sodium carboxymethylcellulose and alkyl or substituted alkylcellulose ethers, stabilizers such as ethylene diamine tetraacetic acid and phosphonic acid derivatives (Dequest ®, fabric softening agents, inorganic salts such as sodium sulphate, and, usually present in very small amounts, fluorescent agents, perfumes, enzymes such as proteases, cellulases, lipases and amylases, germicides and colorants.

The oxygen transfer agents in combination with a peroxygen compound may be useful for removing stains both in consumer type products and for industrial applications. Among consumer products incorporating this invention are laundry detergents, laundry bleaches, hard surface cleaners, toilet bowl cleaners, automatic dishwashing compositions and even denture cleaners. Stained consumer products benefiting from treatment with compositions of this invention may include clothes and other fabrics; household fixtures and appliances such as sinks, toilet bowls and oven ranges; tableware such as drinking glasses, dishes, cookware and utensils; and even dentures. Hair colorants may also be formulated with the bleach composition of this invention. The bleaching system of this invention may also be applied to industrial uses such as for the bleaching of wood pulp.

The system of the present invention may be delivered in a variety of product forms including powders, on sheets or other substrates, in pouches, in tablets, in aqueous liquids, or in non-aqueous liquids such as liquid non-ionic detergents.

The following examples will more fully illustrate the embodiments of this invention. All parts, percentages and proportions referred to herein and in the appended claims are by weight unless otherwise illustrated.

Example 1

Synthesis of N-Sulfonimines

Sulfonimines used for the present invention were prepared by a modified version of procedures set forth by Davis et al. Synthesis of the imines was accomplished by condensing commercially available aromatic aldehydes and sulfonamides. Thus, sulfonimines were prepared by heating equimolar amounts of the requisite sulfonamide and aldehyde in either toluene or chlorobenzene containing a catalytic amount of toluenesulfonic acid. Reaction vessels were either fitted with a drying tube (calcium sulfate) or with a nitrogen flow system. Any water formed from these condensations was removed by equipping the reaction vessels with a Soxhlet extractor containing 3A molecular sieves. Formation of product sulfonimines was monitored by TLC and $^1$H NMR analyses. Complete reaction times varied from 1.5 hours to 2 days. The carboxysulfonimine products were isolated by filtering the reaction mixtures at room temperature. Specific syntheses are outlined in the following examples which focus upon product yield and spectroscopic analyses.

N-Benzylidenebenzenesulfonamide (SULF-13) was prepared by reacting an equimolar mixture of benzenesulfonamide and benzaldehyde diethyl acetal as described by Davis et al in *J. Amer. Chem. Soc.* 1980, 102, 2000.

Example 2

N-(4-Carboxybenzylidene)-4-chlorobenzenesulfonamide (SULF-1)

A well-stirred slurry consisting of 4.64g (31 mmol) of 4-carboxybenzaldehyde and 5.92 g (31 mmol) of 4-chlorobenzenesulfonamide and 20 mg of p-toluenesulfonic acid (TsOH) in 130 mL of toluene was heated to reflux for a total of 5 hours. The water formed from the reaction was removed by a Soxhlet extractor packed with 3A molecular sieves as described above. The mixture was allowed to cool to room temperature and was filtered to provide 9.76 g (98%) of SULF-1 as a white powder: mp >245° C.; IR (Nujol) 3300–2300 (br), 3090, 1689, 1616, 1168, 1013 $cm^{-1}$; $^1$H NMR (DSMO-d6, TMS ext standard, 60 MHz) δ 9.15 (s, 1), 8.01 (s, 4), 7.79 (AB, 4, $J_{AB}$=11, Δγ=16).

Example 3

N-(4-Carboxybenzylidene)benzenesulfonamide (SULF-2)

In a manner similar to Example 2, 1.00 g (6.6 mmol) of 4-carboxybenzaldehyde, 1.05 g (6.6 mmol) of benzenesulfonamide and 20 mg of TsOH in 120 mL of toluene were heated for 2.5 hours to afford 1.82 g (90%) of SULF-2 as a white powder; IR (Nujol) 3400–2400 (br), 1680, 1605, 1283, 1160, 1083 $cm^{-1}$; $^1$H NMR (DMSO-d6, TMS ext std) δ 9.17 (s, 1), 8.1–7.3 (m, 9).

Example 4

N-(4-Chlorobenzylidene)-4-carboxybenzenesulfonamide SULF-3)

In a similar manner to Example 2, 4.00 g (29 mmol) of 4-chlorobenzaldehyde, 5.72 g (29 mmol) of 4-carboxybenzenesulfonamide and 20 mg of TsOH in 150 mL of toluene were heated for 24 hours to provide 6.60 g (71%) of SULF-3 as a light tan powder: IR (Nujol) 3400–2500 (br), 1685, 1595, 1285, 1215, 1005 $cm^{-1}$; $^1$H NMR (DMSO-d6, TMS ext std) δ 9.15 (s, 1), 8.2–7.3 (m, 8).

Example 5

N-Benzylidene-4-carboxybenzenesulfonamide (SULF-4)

In the same manner as Example 2, 4.00 g (38 mmol) of benzaldehyde, 7.58 g (38 mmol) of 4-carboxybenzenesulfonamide and 20 mg of TsOH in 150 mL of toluene were heated for 36 hours to afford 7.40 g (71%) of SULF-4 as a light tan powder: IR (Nujol) 3800–2600 (br), 1685, 1600, 1283, 1155 $cm^{-1}$; $^1$H NMR (DMSO-d6, TMS ext std) δ 9.05 (s, 1), 8.2–7.2 (m, 9).

Example 6

N-(4-Carboxybenzylidene)-4-carboxybenzenesulfonamide (SULF-5)

In the same manner as Example 2, 0.60 g (4 mmol) of 4-carboxybenzaldehyde, 0.80 g (4 mmol) of 4-carboxybenzenesulfonamide and 15 mg of TsOH in 80 mL of chlorobenzene under nitrogen were heated to provide 80% of SULF-5 as a light tan powder: IR (Nujol) 3400–2600 (br), 3082, 1688, 1614, 1160 $cm^{-1}$; $^1$H NMR (DMSO-d6, TMS ext std) δ 9.17 (s, 1), 8.2–7.8 (m, 8).

Example 7

N-(4-Carboxybenzylidene)-3-nitrobenzenesulfonamide (SULF-6)

In a similar manner to Example 2, 2.02 g (10 mmol) of 3-nitrobenzenesulfonamide, 1.50 g (10 mmol) of 4-carboxybenzaldehyde and 20 mg of TsOH in 150 mL of toluene were heated for 5 hours to yield 3.23 g (97%) of SULF-6 as a white powder: IR (Nujol) 3200–2500 (br), 1685, 1554, 1379, 1352, 1165 $cm^{-1}$; $^1$H NMR (DMSO-d6, TMS ext std) δ 9.24 (s, 1), 8.47 (s, 1), 7.9–6.9 (m, 7).

Example 8

N-(4-Cyanobenzylidene)-4-carboxybenzenesulfonamide (SULF-7 )

In a similar manner to Example 2, 1.25 g (9 mmol) of 4-cyanobenzaldehyde, 1.91 g (9 mmol ) of 4-carboxybenzenesulfonamide and 20 mg of TsOH in 150 mL of chlorobenzene under nitrogen were heated for 18 hours to give 2.58 g (86%) of SULF-7 as a white powder: IR (Nujol) 3400–2400 (br), 2224, 1682, 1605, 1155 $cm^{-1}$; $^1$H NMR (DMSO-d6, TMS ext std) δ 9.35 (s, 1), 8.3–7.8 (m, 8).

Example 9

N-(4-Methoxybenzylidene)-4-carboxybenzenesulfonamide (SULF-8)

In a similar manner to Example 2, 1.28 g (9 mmol) of anisaldehyde, 1.89 g (9 mmol) of 4-carboxybenzenesulfonamide and 20 mg of TsOH in 150 mL of chlorobenzene and under nitrogen were heated for 4.5 hours to yield 2.86 g (96%) of SULF-8 as a white powder: IR (Nujol) 3300–2700 (br), 1693, 1601, 1584, 1155 $cm^{-1}$; $^1$H NMR (DMSO-d6, TMS ext std) δ 8.91 (s, 1), 8.4–7.7 (m, 8), 3.92 (s, 3).

Example 10

N-(3-Hydroxybenzylidene)-4-chlorobenzenesulfonamide (SULF-9)

In a similar manner to Example 2, 1.24 g (10 mmol) of 3-hydroxybenzaldehyde, 1.94 g (10 mmol) of 4-chlorobenzenesulfonamide and 20 mg of TsOH in 150 mL of toluene were heated for 12 hours to give 0.29 g (10%) of SULF-9 as a brown powder: IR (Nujol) 3400, 1658, 1556, 1458, 1155, 1025 $cm^{-1}$; $^1$H NMR (DMSO-d6, TMS ext std) δ 8.85 (s,1), 8.73 (s, 1), 7.7–7.2 (m, 8).

Example 11

N-terephthalidene-bis(4-carboxybenzenesulfonamide) (SULF-10)

In a similar manner to Example 2, 0.50 g (4 mmol) of terephthaldicarboxaldehyde, 1.50 g (8 mmol) of 4-carboxybenzenesulfonamide and 20 mg of TsOH in 100 mL of toluene were heated for 18 h to afford 90% of SULF-10 as a fine, light tan powder: IR (Nujol) 3400–2400 (br), 3081, 1689, 1597, 1154, 719 $cm^{-1}$; $^1H$ NMR (DMSO-d6, TMS ext std) δ 9.17 (s, 2), 8.3–7.8 (m, 12).

Example 12

3-Methyl-1,2-benzisothiazole-1,1-dioxide (SULF-11)

This cyclic sulfonimine was prepared by reacting saccharin with 2 equivalents of methyllithium in tetrahydrofuran according to a procedure described in the *Journal of the Chemical Society, Perkin I,* 2589 (1974).

Example 13

N-(3-Pyridinylmethylene)-4-chlorobenzenesulfonamide (SULF-12)

In a similar manner to Example 2, 18.5 mmol of 3-pyridinecarboxaldehyde, 18.5 mmol of 4-chlorobenzenesulfonamide and 20 mg of TsOH in 100 mL of toluene reacted under reflux conditions to afford SULF-12 in 65% yield and high purity: $^1H$ NMR (DSMO-$d_6$, TMS ext std) δ 9.3 (s,1), 9.2 (d, 1), 8.9 (m, 1), 8.4 (m, 1), 8.0–7.8 (AB. 4).

Example 14

Activation of Monopersulfate and Peracids by Sulfonimines

Bleaching studies were conducted by comparing the performance of a common bleach (such as monopersulfate) with and without the presence of sulfonimine. In this regard, the stain removal observed without the intervention of sulfonimines served as an experimental blank and the amount of stain removal by the sulfonimine containing system constituted activation of a given bleach.

Stain bleaching experiments were conducted in a Terg-O-Tometer in 500 mL of milli-Q water using two tea-stained cotton cloths measuring 3×4 inches. In a typical test, 0.75 g of Surf ® was added to the system and the pH of the solution was constantly buffered to the indicated level by the addition of dilute aqueous sodium hydroxide or hydrochloric acid. A given oxidant was added to the system followed by an appropriate amount of sulfonimine. Washes were carried out at 40° C. for 15 minutes.

Stain bleaching was measured reflectometrically using a Colorgard System/05 Reflectometer. Bleaching was indicated by an increase in reflectance, reported as ΔR. In general, a ΔR of one unit is perceivable in a paired comparison while a ΔR of two units is perceivable monadically.

Results of activation using SULF-1 with OXONE ® (ex DuPont, a trisalt of the following composition $2KHSO_5/KHSO_4/K_2SO_4$) are reported in Table I. As can be seen, a relatively high level of monopersulfate (about 100 ppm active oxygen) provided only 3.2 units of bleaching. However, when accompanied by a low level of sulfonimine the overall bleaching performance was elevated to 12.2 units, an activation of 280% over monopersulphate alone.

In a similar experiment, peracetic acid (about 50 ppm active oxygen) provided only 3.1 units of bleaching. The effectiveness was increased to 12.9 units by inclusion of a low level of SULF-1. The stable peracid H48 (monoperoxyphthalic acid, magnesium salt hexahydrate) displayed no stain removal on its own. However, when accompanied by only $3\times10^{-4}$M sulfonimine, almost 4 units of activation occurred. Analogously, the bleaching performance of the stable diperoxydodecanedioic acid (DPDA) was essentially doubled by incorporating a small amount of SULF-1.

TABLE 1

| Activations Using SULF-1 | | | | | |
|---|---|---|---|---|---|
| "O" Source | pH | [SULF] $\times10^{-4}$M | ["O"] $\times10^{-4}$M | ΔR "O" | ΔR SULF |
| Oxone ($KHSO_5$) | 8.5 | 6.2 | 52.0 | 3.2 | 12.2 |
| Peracetic Acid | 9–10 | 6.2 | 31.0 | 3.1 | 12.9 |
| H48 | 9.5 | 3.0 | 4.8 | −0.7 | 3.4 |
| DPDA | 9.5 | 3.0 | 3.0 | 3.4 | 6.1 |

A hydrophobic spaghetti stain was prepared by treating cotton cloths with spaghetti sauce. Removal of this stain was measured reflectometrically as described above, Bleaching of this oily stain is reported as ΔΔB, i.e, ΔΔB=(Reflectance of stained fabric washed with sulfonimine/H48-reflectance of stained fabric before washing)—(reflectance of stained fabric washed with H48 alone—reflectance of stained fabric before washing), The results using N-Benzylidenebenzenesulfonamide (SULF-13) as activator in conjunction with 4.8x10–4M H48 in Surf at pH 9.5 and 40° C. (15 minute wash time) are shown in Table II.

TABLE II

| Bleaching of Spaghetti Stain by SULF-13/H48 System | |
|---|---|
| [SULF] $\times10^{-4}$M | ΔΔB |
| 3.0 | 2.7 |
| 1.0 | 2.4 |
| 0.5 | 1.6 |

From the above results it is demonstrated that simple common oxidants give rise to enhanced bleaching brought about by the inclusion of relatively small amounts of sulfonimines.

The foregoing description and Examples illustrate selected embodiments of the present invention. In light thereof, various modifications will be suggested to one skilled in the art all of which are within the spirit and purview of this invention.

What is claimed:

1. A compound whose structure is:

$$R^1R^2C=NSO_2R^3$$

wherein:

$R^1$ may be a substituted or unsubstituted radical selected from the group consisting of hydrogen, phenyl, aryl, alkyl and cycloalkyl radicals;

$R^2$ may be a substituted or unsubstituted radical selected from the group consisting of hydrogen, phenyl, aryl, alkyl, cycloalkyl $R^1C=NSO_2R^3$ nitro, halo, cyano, alkoxy, keto, carboxylic and carboalkoxy radicals;

$R^3$ may be a substituted or unsubstituted radical selected from the group consisting of phenyl, aryl, alkyl, cycloalkyl, nitro, halo, and cyano radicals;

$R^1$ with $R^2$ and $R^2$ with $R^3$ may respectively together form a cycloalkyl and aromatic ring system; and wherein at least one of $R^1$, $R^2$, $R^3$ contains a water-solubilizing functional unit selected from the group consisting of carboxylic acid, phosphoric acid, phosphonic acid, sulfuric acid, sulfonic acid, $C_1$–$C_{40}$, quaternary di- or tri-alkyl ammonium radicals and salts thereof and said substitution of $R^1$, $R^2$, $R^3$, is a functional unit selected from the group consisting of nitro, halo, cyano, $C_1$–$C_{20}$ alkyl, amino, aminoalkyl, thioalkyl, sulfoxyalkyl, carboxyester, hydroxy, $C_1$–$C_{20}$ alkoxy, polyalkoxy, $C_1$–$C_{40}$ quaternary di- or tri-alkyl ammonium radicals and mixtures thereof.

2. A compound according to claim 1 which is N-(4-carboxybenzylidene)-4-chlorobenzenesulfonamide.

3. A compound according to claim 1 which is N-(4-carboxybenzylidene)benzenesulfonamide.

4. A compound according to claim 1 which is N-(4-chlorobenzylidene)-4-carboxybenzenesulfonamide.

5. A compound according to claim 1 which is N-benzylidene-4-carboxybenzenesulfonamide.

6. A compound according to claim 1 which is N-(4-carboxybenzylidene)-4-carboxybenzenesulfonamide.

7. A compound according to claim 1 which is N-(4-carboxybenzylidene)-3-nitrobenzenesulfonamide.

8. A compound according to claim 1 which is N-(4-cyanobenzylidene)-4-carboxybenzenesulfonamide.

9. A compound according to claim 1 which is N-(4-methoxybenzylidene)-4-carboxybenzenesulfonamide.

10. A compound according to claim 1 which is N-(3-hydroxybenzylidene)-4-chlorobenzenesulfonamide.

11. A compound according to claim 1 which is N-terephthalidene-bis(4-carboxybenzenesulfonamide).

12. A compound according to claim 1 wherein said water-solubilizing functional unit is a $C_1$–$C_{40}$ quaternary ammonium radical.

* * * * *